US010000380B2

(12) United States Patent
Barnicki et al.

(10) Patent No.: US 10,000,380 B2
(45) Date of Patent: Jun. 19, 2018

(54) METHOD FOR THE MANUFACTURE OF POLYMERIC SULFUR

(71) Applicant: EASTMAN CHEMICAL COMPANY, Kingsport, TN (US)

(72) Inventors: Scott Donald Barnicki, Kingsport, TN (US); Robert Thomas Hembre, Johnson City, TN (US); Michael Richard Laningham, Erwin, TN (US); Sumit Chakraborty, Johnson City, TN (US); Venkateswarlu Bhamidi, Kingsport, TN (US)

(73) Assignee: EASTMAN CHEMICAL COMPANY, Kingsport, TN (US)

( * ) Notice: Subject to any disclaimer, the term of this patent is extended or adjusted under 35 U.S.C. 154(b) by 0 days. days.

(21) Appl. No.: 15/440,007

(22) Filed: Feb. 23, 2017

(65) Prior Publication Data
US 2017/0253483 A1 Sep. 7, 2017

Related U.S. Application Data

(60) Provisional application No. 62/302,213, filed on Mar. 2, 2016.

(51) Int. Cl.
*C01B 17/12* (2006.01)
*C07D 341/00* (2006.01)
*C01B 17/02* (2006.01)

(52) U.S. Cl.
CPC ...... *C01B 17/0253* (2013.01); *C01B 17/0243* (2013.01); *C01B 17/12* (2013.01); *C07D 341/00* (2013.01)

(58) Field of Classification Search
CPC . C01B 17/0243; C01B 17/12; C01B 17/0253; C07D 341/00
See application file for complete search history.

(56) References Cited

U.S. PATENT DOCUMENTS

| | | | |
|---|---|---|---|
| 1,875,372 A | 9/1932 | Endres | |
| 2,419,309 A | 4/1947 | Belchetz | |
| 2,419,310 A | 4/1947 | Belchetz | |
| 2,460,365 A | 2/1949 | Schallis | |
| 2,462,146 A | 2/1949 | Walcott et al. | |
| 2,513,524 A | 7/1950 | Schallis | |
| 2,534,063 A | 12/1950 | Ross et al. | |
| 2,757,075 A | 7/1956 | Haimsohn | |
| 3,844,941 A | 10/1974 | Jones | |
| 3,891,743 A | 6/1975 | Block | |
| 4,017,467 A | 4/1977 | Doss | |
| 4,238,470 A | 12/1980 | Young | |
| 4,242,472 A | 12/1980 | Hoshino et al. | |
| 4,740,559 A | 4/1988 | Johansson et al. | |
| 4,752,507 A | 6/1988 | Johansson et al. | |
| 4,870,135 A | 9/1989 | Mowood et al. | |
| 6,319,993 B2 | 11/2001 | Weidenhaupt et al. | |
| 6,420,581 B1 | 7/2002 | Lodaya et al. | |
| 6,441,098 B2 | 8/2002 | Halko et al. | |
| 7,569,639 B2 | 8/2009 | Choi et al. | |
| 7,662,874 B2 | 2/2010 | Korth et al. | |
| 8,859,719 B2 | 10/2014 | Mohamed et al. | |
| 2014/0116594 A1 | 5/2014 | Miyazaki | |
| 2014/0200383 A1 | 7/2014 | Marks et al. | |
| 2014/0213708 A1 | 7/2014 | Kushida | |
| 2017/0253484 A1 | 9/2017 | Barnicki et al. | |

FOREIGN PATENT DOCUMENTS

| | | | |
|---|---|---|---|
| CN | 101 837 958 A | 9/2010 | |
| CN | 103 601 156 A | 2/2014 | |
| EP | 0846722 B1 | 4/2002 | |
| EP | 1500630 A2 * | 1/2005 | ............. C01B 17/12 |
| EP | 2128153 B1 * | 8/2013 | ........... C07D 341/00 |
| WO | WO 2003060002 | 7/2003 | |

OTHER PUBLICATIONS

PCT International Search Report and Written Opinion dated May 11, 2017 for International Application No. PCT/US2017/019888.
Office Action dated Jun. 30, 2017 received in co-pending U.S. Appl. No. 15/015,165.
Copending U.S. Appl. No. 15/659,094, filed Jul. 25, 2017, Barnicki et al.
PCT International Search Report and Written Opinion dated Apr. 19, 2017 for International Application No. PCT/US2017/019881.
Steudel, Ralph et al, "A New Allotrope of Elemental Sulfur: Convenient Preparation of cyclo-S 14 from S 8", Angew. Chem. Int. Ed., Jan. 1, 1998, pp. 2377-2378.
Moeckel, Herman, "Separation of dihydrogen polysulfides (polysulfanes) using reversed-phase HPLC", Fresenius' Zeitschrift Fuer Analytische Chemie, vol. 318, No. 2, 1984, pp. 116-120.
Zysman-Colman, Eli et al., "Probing the chemistry of rare sulfur allotropes: S9, S12 and S20", Journal of Sulfur Chemistry, vol. 29, No. 3-4, 2008, pp. 309-326.
ASTM D1993-03 (2013).
Bueno-Ferrer et at., Journal of Rare Earths, 28, 2010, "Relationship between surface area and crystal size of pure and doped cerium oxides", pp. 647-653.
Chen et al., "Quantitative Analysis of Powder Mixtures by Raman Spectrometry: the influence of particle size and its correction", Analytical Chemistry, 84, 2012, pp. 4088-4094.
Choi et al. "Thermal Aging Behaviors of Elemental Sulfur-Free Polyisoprene Vulcanizates" *Bull. Korean Chem Soc.*, Col. 26, 2005, pp. 1853-1855.
Eckert et al. "Elemental Sulfur and Sulfur-Rich Compounds" *Springer*, 2003, pp. 10-54.
Leste-Lasserre, Pierre "Sulfur Allotrope Chemistry" *McGill University*, 2001, pp. 119-132.
Masamichi Ikeda et al., Radioisotopes, "Measurements of Sulfure Solubility and Diffusibility in Rubber by Tracer Method", vol. 20, No. 10, p. 556, (1973).
Mausle, H.J.; Steudel, R., "Simple preparation of Cyclohexasulfur (S6) from dichlorodisulfane (S2Cl2) and ionic iodides", Z. anorg, allg. Chem. 463, 1980, pp, 27-31.

(Continued)

Primary Examiner — Timothy C Vanoy
(74) Attorney, Agent, or Firm — Michael K. Carrier

(57) ABSTRACT

The present invention relates to a method for the manufacture of polymeric sulfur. The method includes reacting a metallasulfur derivative with an oxidizing agent to form polymeric sulfur.

14 Claims, No Drawings

(56) References Cited

OTHER PUBLICATIONS

Steudel, R.; Strauss, R.; Koch, L., "Quantitative HPLC Analysis and Thermodynamics of Sulfur Melts", Angew, Chem. Int. Ed. Engl., 24(1), 1985, pp. 59-60.

Steudel, R.; Mausle, H.-J., "Detection of Large-Ring Sulfur Molecules in Liquid Sulfur Simple Preparation of S12, α-S18, S20 from S8", Angew. Chem, Int. Ed. Engl., 18(2), 1979, pp. 152-153.

Steudel, R.; Eckert, B., "Solid Sulfur Allotrope", Topics in Current Chemistry (2003), 230, pp. 1-79.

Steudel et al., "Infrared and Raman Spectra of Cyclo Dodecasulphur" Journal of Molecular Spectroscopy, 51, 1974, pp. 189-193.

Schmidt, M.; Block, H.-D, "Occurrence of Cyclododecasulfur in Sulfur Melts", Angew. Chem. Int. Ed. Engl, 6(11), 1967, pp. 955-956.

Schmidt, M.; Wilhelm, E., "Cyclodocecasulfur, S12", Angew. Chem. Int. Ed. Engl., 5(11), 1966, pp. 964-965.

Steudel, R.; Steidel, J.; Sandow, T., "Representation, Crystal Structure and Vibrational Spectra of CycloUndecasulfur and Cyclotridecasulfur", Z. Natureforsch B 1986, 41, pp. 958-970.

Schmidt, M.; Knippschild, G.; Wilhelm, E., "Memorandum on a Simplified Synthesis of Cyclododecasulfure $S_{12}$" Chem. Ber., 101 1968, p. 381-382.

Schmidt, M.; Block, B.; Block, H.D.; Kopf, H.; Wilhelm, E., "Cycloheptasulfur, S7, and Cycladocecasulfur, S10—Two New Sulfur Rings", Angew. Chem. Int. Ed. Engl., 7(8), 1968, pp. 632-633.

Inorganic Chemistry by Duward Shriver, P.W. Atkins and Cooper Langford, W. H. Freeman & Co, 1990, pp. 407-408.

Copending U.S. Appl. No. 15/015,165, filed Feb. 4, 2016, Barnicki, et al.

Office Action dated Jul. 5, 2016 received in co-pending U.S. Appl. No. 15/015,165.

Office Action dated Jan. 13, 2017 received in co-pending U.S. Appl. No. 15/015,165.

Copending U.S. Appl. No. 15/440,056, filed Feb. 23, 2017, Barnicki, et al.

Steudel, Ralf, "Elemental Sulfur and Related Homocyclic Compounds and Ions", Studies in Inorganic Chemistry, 1984, v5, p. 3.

PCT International Search Report and Written Opinion dated Mar. 23, 2017 for International Application No. PCT/US2016/067695.

Steudel et al, Thermal Polymerization and Depolymerization Reactions of 10 Sulfer Allotropes Studied by HPLC and DSC, vol. 517, No. 10, pp. 7-42, Oct. 1, 1984.

Buskirk, P.R. Van, et al, Practacle Parameters for Mixing, Rubber Chemistry and Technology, vol. 48, pp. 577-591, May 1975.

Kim, Pan Soo, et al, Flow Visualization of Intermeshing and Separated Counter-Rotating Rotor Internal Mixer, Rubber Chemistry and Technology, vol. 67, pp. 880-891, Apr. 1994.

Manas-Zloczower, I. et al, Dispersive Mixing in Internal Mixers—A Theoretical Model Based on Agglomerate Rupture, vol. 55, pp. 1250-1285, 1982.

Office Action dated Nov. 24, 2017 received in co-pending U.S. Appl. No. 15/440,056.

\* cited by examiner

METHOD FOR THE MANUFACTURE OF POLYMERIC SULFUR

CROSS-REFERENCE TO RELATED APPLICATIONS

This application claims the benefit of U.S. Provisional Patent Application Ser. No. 62/302,213 filed on Mar. 2, 2016, the disclosure of which is incorporated herein by reference in its entirety.

FIELD OF THE INVENTION

The present invention relates generally to a method for the manufacture of polymeric sulfur.

BACKGROUND OF THE INVENTION

Polymeric sulfur (often referred to as "insoluble sulfur" because of its extremely low solubility in carbon disulfide as compared to cyclooctasulfur) and routes for its synthesis from sulfur-containing moieties have been described in the literature. For example, polymeric sulfur, also referred to herein as polymer, is known to be present in thermally equilibrated sulfur allotrope mixtures in concentrations dependent on the equilibration temperature, ranging from about 0.30 wt % or less at a temperature less than about 140° C. to a maximum of about 40 wt % between 200 and 300° C. (see Steudel, R.; Strauss, R.; Koch, L., "Quantitative HPLC Analysis and Thermodynamics of Sulfur Melts", Angew. Chem. Int. Ed. Engl., 24(1), 1985, pp. 59-60).

Numerous US patents describe methods for polymer synthesis (see for example Belchetz, U.S. Pat. No. 2,419,309; Belchetz, U.S. Pat. No. 2,419,310; Schallis, U.S. Pat. No. 2,513,524; and Ross et al, U.S. Pat. No. 2,534,063). All involve vaporizing sulfur at high temperatures (generally above about 400° C., forming an equilibrium mixture comprising 20-40 wt % polymeric sulfur, cyclooctasulfur, and other cyclic sulfur allotropes, and then rapidly quenching the equilibrium mixture in a solvent, such as carbon disulfide, at low temperature (generally less than 60° C.) to produce a crude polymer-containing-mixture. The polymer-containing mixture is then typically extracted with solvent, for example carbon disulfide, to remove soluble sulfur impurities, for example cyclooctasulfur. After quenching and extraction the polymeric sulfur is initially amorphous but tends to convert to a microcrystalline form with residence in the solvent.

Prior art methods for manufacturing polymer all suffer from one or more drawbacks such as low per pass yields, multiple convoluted manufacturing steps requiring the use of dangerous solvents (such as carbon disulfide), and have very high energy usage because of high temperatures needed for thermal polymer formation and the rapid low temperature quench needed to preserve polymer formation. A continuing need therefore exists for a low energy, high-yield, safe, and cost-effective method for the manufacture of cyclic sulfur allotropes that meets industrial criteria for commercial implementation.

SUMMARY OF THE INVENTION

The present invention relates to a method for the manufacture of polymeric sulfur (also referred to herein as "polymer"). The method includes reacting a metallasulfur derivative with an oxidizing agent in a reaction zone to form a polymer-containing reaction mixture that contains the polymeric sulfur. The method preferably further includes isolating the polymer from the polymer-containing reaction mixture. The method of the present invention is particularly useful for the manufacture of a polymeric sulfur that is useful in vulcanizing compositions for use in forming a vulcanized article.

Further aspects and areas of applicability will become apparent from the description provided herein. It should be understood that the description and specific examples are intended for purposes of illustration only and are not intended to limit the spirit and scope of the present invention.

DETAILED DESCRIPTION

As utilized herein, the following terms or phrases are defined as follows:

"Polymeric Sulfur" or "Sulfur Polymer" or just "Polymer" means a sulfur compound comprising a mixture of chain-like macromolecules of sulfur atoms and very large homocyclic rings of $S_n$ sulfur atoms, for example wherein n is greater than about 24, or greater than about 30, or greater than about 50, that is, n>24, 30, or 50.

"Cyclic Sulfur Allotrope" means a sulfur compound characterized by a homocyclic ring of sulfur atoms.

"Cyclododecasulfur compound" means a cyclic sulfur allotrope with twelve sulfur atoms in its homocyclic ring, also referred to herein as 812.

"Metallasulfur derivative" means a compound containing divalent sulfur (S) atoms and metal (M) atoms with a ratio of sulfur to metal atoms of at least 2:1 (S:M≥2.0). The defining structural unit of such derivatives may be represented as:

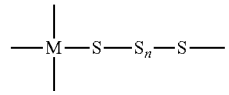

In which the metal atom (M) may be divalent or multivalent and the sulfur atoms (S) are divalent and form a chain with n≥0. The compound may be linear or branched, it may be cyclic, multicyclic, oligomeric or polymeric and it may contain other elements, ligands, cations or anions bonded or coordinated to the metal atom (inner- or outer-sphere), without limitation.

"Metallacylcosulfane" means a metallasulfur derivative with at least one cyclic structural feature containing sulfur and metal atoms, preferably only sulfur and metal atoms, with at least two sulfur atoms and one or more metal atoms.

"Sulfur templating agent" or "Sulfur templating agents" mean a compound, or a combination of compounds and elements which, when reacted with elemental sulfur, form a metallasulfur derivative.

"Oxidizing agent" means an agent which is (i) reduced by a metallasulfur derivative; (ii) promotes the release of the sulfur contained in the metallasulfur derivative and (iii) may or may not add sulfur from its composition to the polymeric sulfur being produced in the process.

"Pseudohalogen" means a molecule or functional group with properties and a reactivity profile similar to a halogen (see e.g. Inorganic Chemistry by Duward Shriver, P. W. Atkins and Cooper Langford, W. H. Freeman & Co., 1990, pp 407-408).

The present invention is a method for producing polymeric sulfur as described herein. Similar methods may be used for the manufacture of cyclic sulfur allotropes wherein the number of sulfur (S) atoms in the allotrope's homocyclic ring is selected from the group consisting of 10, 12, 15, 18, 20 and 24, and especially cyclododecasulfur, methods for which are disclosed and claimed in a copending application, filed herewith and having common assignee. The method of the present invention includes reacting a metallasulfur derivative with an oxidizing agent. A suitable metallasulfur derivative is characterized by the formula

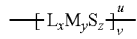

[I]$_w$ wherein
L is a monodentate or polydentate ligand species which may be the same or different when x>1;
x is the total number of ligand species L and is from 0 to 6 inclusive;
M is a metal atom;
y is the total number of metal atoms and is from 1 to 4 inclusive;
S is a sulfur atom;
z is the number of sulfur atoms, and is from 1 to 12 inclusive;
u represents the charge of the metallasulfur derivative and may be from −6 to +6 inclusive;
v is the number of metallasulfur derivative units in an oligomeric or polymeric structure;
I is an ionic atom or group and may be cationic or anionic;
and w is the number of cationic or anionic atoms or groups, as required to provide charge neutrality.

The ligand species may be mono- or polydentate and may be charged or neutral. Suitable ligand species are cyclopentadienyl or substituted cyclopentadienyl rings; amines such as primary, secondary, and tertiary alkyl or aryl linear or cyclic amines and may also be diamines or triamines or other polyamines such as ethylenediamine and ethylenetriamine and their derivatives, piperidine and derivatives, and pyrrolidine and derivatives; or heteroaromatic derivatives such as pyridine and pyridine derivatives or imidazole and imidazole derivatives. Preferred amines include but are not limited to tetraalkyl ethylenediamines, such as tetramethyl ethylenediamine (TMEDA), tetraethyl ethylenediamine, tetrapropyl ethylenediamine, tetrabutyl ethylenediamine; diethylene-triamine and derivatives such as pentamethyldiethylenetriamine (PMDETA); pyridine and derivatives of pyridine, such as bipyridine, 4-(N,N-dimethylaminopyridine (DMAP), picolines, lutidines, quinuclidines; imidazole and derivatives of imidazole such as N-methylimidazole, N-ethylimidazole, N-propylimidazole, and N-butylimidazole.

Suitable metals for the substituent M above include copper, zinc, iron, nickel, cobalt, molybdenum, manganese, chromium, titanium, zirconium, hafnium, cadmium, mercury; and precious and rare earth metals such as rhodium, platinum, palladium, gold, silver, and iridium. A preferred metal is zinc.

Particularly suitable metallasulfur derivatives for the method of the present invention are metallacyclosulfanes. Preferred metallacyclosulfanes include those depicted below as A, B, C and D. Other metallasulfur derivatives are oligomeric or polymeric species and may be linear as depicted in E below or branched as depicted in F below with the metal atoms serving as branch points.

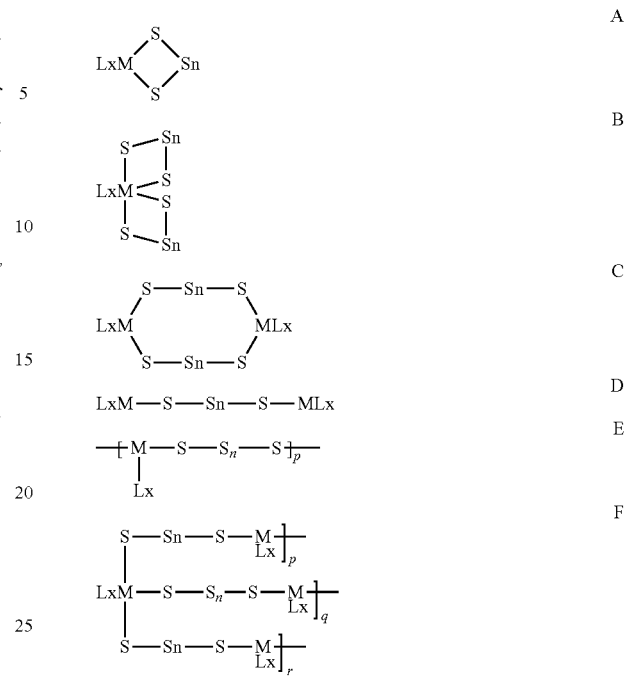

Metallasulfur derivatives may contain charged ligand species. For instance, a suitable metallasulfur derivative for the formation of a cyclododecasulfur compound is shown below:

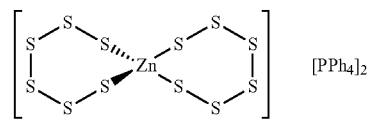

It contains only sulfur atoms bonded to zinc in two metallacyclosulfane rings and two tetraphenyl phosphonium ion groups to neutralize the dianionic charge of the metallasulfur derivative.

A related metallasulfur derivative which contains ligands is illustrated below:

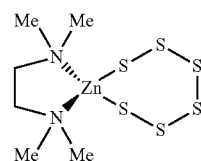

In this case a TMEDA ligand coordinated to zinc replaces a hexasulfide dianion, and thus the metallasulfur derivative is not anionic, it is neutral.

A preferred class of metallacyclosulfanes for the method of the present invention are those containing an N-donor zinc complex. Such complexes are formed by reacting elemental sulfur, also referred to herein as cyclooctasulfur or S$_8$, with metallic zinc in a solvent composed of, or containing, a donor amine, diamine or polyamine templating agent as described in more detail below. Examples of N-donor-zinc-cyclosulfanes include (TMEDA)Zn(S$_6$), (DMAP)$_2$Zn(S$_6$), (pyridine)$_2$Zn(S$_6$), (methylimidazole)$_2$Zn(S$_6$), (quinuclidine)$_2$Zn(S$_6$), (PMDETA)Zn(S$_4$), and (bipyridine)$_2$Zn(S$_6$). The zinc complex, (TMEDA)Zn(S$_6$), is a particularly preferred metallacyclosulfane in the method of the present invention and can be formed by reacting cyclooctasulfur, tetramethylethylenediamine and zinc. We have found that the the metallacyclosulfane-froming reactions are best accomplished in the presence of water, as in Example 14 in which the addition of water consistently produced (TMEDA)Zn(S$_6$) complex in high yields and purity even with low grade TMEDA.

U.S. Pat. No. 6,420,581, the disclosure of which is incorporated herein by reference in its entirety, relates to processes of producing zinc hexasulfide amine complexes that are suitable for use according to the present invention. These processes comprise reacting zinc, sulfur and a molar excess of amine at an elevated temperature to obtain a reaction mixture comprising zinc hexasulfide amine complexes and excess amine. A first solvent in which the zinc hexasulfide amine complexes are largely not soluble is added to obtain a slurry of the reaction mixture. The zinc hexasulfide amine complexes may be recovered in a subsequent separation process.

Another preferred class of metallacyclosulfanes for the method of the present invention are those containing metallocene complexes of metals such as titanium, zirconium, hafnium, or nickel, that is, Cp$_2$M(S$_5$). Other metallacyclosufanes with a number of transition metals or main group metals are useful and are known (see Takeda, N; Tokitoh, N.; Okazaki, R. "Polysulfido Complexes of Main Group and Transition Metals" *Topics in Current Chemistry*, 231, 2003, pp 153-202). The examples of Takeda, et al. are illustrative of preferred metallacyclosulfanes types (A, B, and C) depicted above. This range of metals and diverse metallasulfurane structural types are included herein as examples of suitable metallasulfur derivatives. Many different metals and ligand types may also be assembled into complexes, oligomers or polymers with related metallasulfur structures (as in A-F), and these are incorporated, without limitation, within the scope of the invention. The metallasulfur derivatives of the method of the present invention may be formed by reacting elemental sulfur with a sulfur templating agent. Accordingly, in a preferred embodiment, the method of the present invention includes the step of reacting elemental sulfur with a sulfur templating agent to form a metallasulfur derivative prior to the step of reacting the metallasulfur derivative with an oxidizing agent.

Suitable sulfur templating agents for use in this embodiment of the method of the present invention include those characterized by the formula:

wherein

L is a monodentate or polydentate ligand species which may be the same or different when x>1;

x is the total number of ligand species L and is from 1 to 6 inclusive;

M is a metal atom; and y is the total number of metal atoms and is from 1 to 4 inclusive.

The ligand species may be mono- or polydentate. Suitable ligand species are cyclopentadienyl or substituted cyclopentadienyl rings; amines such as primary, secondary, and tertiary alkyl or aryl linear or cyclic amines and may also be diamines or triamines or other polyamines such as ethylenediamine and ethylenetriamine and their derivatives, piperidine and derivatives, and pyrrolidine and derivatives; or heteroaromatic derivatives such as pyridine and pyridine derivatives or imidazole and imidazole derivatives.

Preferred amines include but are not limited to tetraalkyl ethylenediamines, such as tetramethyl ethylenediamine (TMEDA), tetraethyl ethylenediamine, tetrapropyl ethylenediamine, tetrabutyl ethylenediamine; diethylene-triamine and derivatives such as pentamethyldiethylenetriamine (PMDETA); pyridine and derivatives of pyridine, such as bipyridine, 4-(N,N-dimethylaminopyridine (DMAP), picolines, lutidines, quinuclidines; imidazole and derivatives of imidazole such as N-methylimidazole, N-ethylimidazole, N-propylimidazole, and N-butylimidazole.

Suitable metals for the substituent M above include copper, zinc, iron, nickel, cobalt, molybdenum, manganese, chromium, titanium, zirconium, hafnium, cadmium, mercury; and precious and rare earth metals such as rhodium, platinum, palladium, gold, silver, and iridium. A preferred metal is zinc.

In the method of the present invention, the above-described metallasulfur derivative is reacted with an oxidizing agent. An appropriate oxidizing agent is any agent which is reduced by a metallasulfur derivative and promotes the release of the sulfur contained in the metallasulfur derivative. In addition, the oxidizing agent may or may not add sulfur from its composition to the polymeric sulfur being produced in the process. Thus, in one aspect, sulfur atoms from the oxidizing agent are added to the polymeric sulfur, while in another aspect, any sulfur atoms in the oxidizing agent are not added to the polymeric sulfur being produced.

Non-limiting examples of suitable oxidizing agents include those of the formula:

wherein X and X' are the same or different and are selected from the group consisting of halogens and pseudohaolgens. Preferably, X and X' are either both chlorine or bromine and accordingly the oxidizing agent for the method of the present invention is either molecular bromine (Br$_2$) or molecular chlorine (Cl$_2$). X and X' may also be pseudohalogen groups such as cyanide, thiocyanide, sulfate, thiosulfate, sulfonate or thiosulfonate. In the embodiment where the pseudohalogen groups are cyanide or thiocyanide, the oxidizing agent X—X' would be dicyanogen or dithiocyanogen, respectively. In another embodiment wherein the pseudohalogen groups are sulfate, thiosulfate, sulfonate or thiosulfonate, it will be understood that the corresponding persulfate or perthiosulfate typically does not transfer sulfur atoms to the polymeric sulfur being produced, although in one aspect, the present invention does not exclude that possibility.

Another suitable oxidizing agent is molecular oxygen (O$_2$). When molecular oxygen is the oxidizing agent X and X' above are oxygen atoms. In the embodiment where the oxidizing agent is molecular oxygen, the molecular oxygen may, or may not, require the addition of a catalyst which promotes and/or accelerates the rate of electron transfer from the sulfur in the metallasulfur derivative to the oxidant, such that the oxidizing agent may include molecular oxygen and a catalyst. Such catalysts may be metals or metal complexes and examples of such complexes include the complexes of Fe(II), but other metals such as manganese, vanadium, molybdenum and copper are also common. Any substance which, in combination with molecular oxygen, will induce the desired oxidation of a metallasulfur derivative is within the scope of catalyst as described herein.

While the oxidizing agent for the method of the present invention has been described above in the context of suitable chemical compounds, it will be understood by a person of ordinary skill that, in general, electrochemically generated oxidants are capable of acting as oxidizing agents and may therefore be useful oxidizing agents in the method of the present invention. Examples include hydrogen peroxide, alkyl- and acyl peroxides, halogen atom radicals, and high oxidation state metal-centered oxidants such as Ce(IV) and Ir(V). Anodic oxidation of metallasulfur derivatives may include a catalyst at the anode to enable facile and selective oxidation. Such species may be used in combination with or in conjunction with molecular oxygen as the oxidizing agent for the method of the present invention.

Yet other suitable oxidizing agents are sulfuryl halides such as $SO_2Cl_2$ and $SO_2Br_2$; and halosulfides, such as $SnCl_2$ and $SnBr_2$ wherein n is greater than or equal to one. Examples of the latter include $SCl_2$, $S_2Cl_2$, $SBr_2$, $S_2Br_2$, and the like. Certain of these oxidizing agents, unlike some others useful according to the invention, may contribute sulfur atoms to the polymeric sulfur produced.

In the method of the present invention, the stoichiometry of the oxidizing agent to the metallasulfur derivative may depend on the composition and structure of the metallasulfur derivative. In one embodiment of the method of the present invention, the stoichiometric ratio of the oxidizing agent to the metallasulfur derivative is selected so that one equivalent of oxidizing agent (X—X') is present for every two M-S bonds in the metallasulfur derivative. For example, for the production of polymeric sulfur, if the metallasulfur derivative has one metal-sulfur bond for every three sulfur atoms then one equivalent of an oxidizing agent X—X' is combined with a weight of metallasulfur derivative equal to six equivalents of sulfur. Examples of suitable ratios of oxidizing agent to metallasulfur derivative include: 1 mole of $(TMEDA)Zn(S_6)$ to 1 mole of $Br_2$; 1 mole of $(TMEDA)Zn(S_6)$ to 1 mole of $Cl_2$; 1 mole of $(C_5H_5)_2Ti(S_5)$ to 1 mole of $Cl_2$; 1 mole of $[PPh_4]_2[Zn(S_6)_2]$ to 2 moles of $Br_2$; 1 mole of $[PPh_4]_2[Zn(S_6)_2]$ to 2 moles of $Cl_2$; 1 mole of (N-methyl imidazole)$_2$Zn(S$_6$) to 1 mole of $Br_2$; 1 mole of (N-methyl imidazole)$_2$Zn(S$_6$) to 1 of mole $Cl_2$; 1 mole of (PMDETA)Zn(S$_4$) to 1 mole of $Br_2$.

In another aspect of the method of the present invention, the stoichiometry of the oxidizing agent (X—X') to the metallasulfur derivative may be selected so as to increase the purity of the final polymer product. Thus, in a preferred embodiment, a substoichiometric (i.e. less than one equivalent) ratio of the oxidizing agent to the metallasulfur derivative is selected in order to synthesize a polymer-containing mixture having lower levels of halogens. In this aspect, the stoichiometric ratio of the oxidizing agent to the metallasulfur derivative is selected so that less than one equivalent of the oxidizing agent is present for every two M-S bonds in the metallasulfur derivative. For the production of a polymer compound, if the metallasulfur derivative has one metal-sulfur bond for every three sulfur atoms, then substoichiometric amounts of an oxidizing agent X—X' may be combined with a weight of metallasulfur derivative equal to six equivalents of sulfur. In this aspect, examples of suitable ratios of oxidizing agent to metallasulfur derivative include: 1 mole of $(TMEDA)Zn(S_6)$ to 0.90-0.99 mole of $Br_2$; 1 mole of $(TMEDA)Zn(S_6)$ to 0.90-0.99 mole of $Cl_2$; 1 mole of $(C_5H_5)_2Ti(S_5)$ to 0.90-0.99 mole of $Cl_2$; 1 mole of $[PPh_4]_2[Zn(S_6)_2]$ to 1.80-1.99 moles of $Br_2$; 1 mole of $[PPh_4]_2[Zn(S_6)_2]$ to 1.80-1.99 moles of $Cl_2$; 1 mole of (N-methyl imidazole)$_2$Zn(S$_6$) to 0.90-0.99 mole of $Br_2$; 1 mole of (N-methyl imidazole)$_2$Zn(S$_6$) to 0.90-0.99 mole $Cl_2$; 1 mole of (PMDETA)Zn(S$_6$) to 0.90-0.99 mole of $Br_2$.

The method of the present invention is a method for the manufacture of polymeric sulfur. In one embodiment, a preferred metallasulfur derivative is a tetramethylethylene-diamine/Zn(S$_6$) complex. The tetramethylethylene-diamine/Zn(S$_6$) complex is most preferably formed in situ by reacting tetramethylethylenediamine and zinc in the presence of elemental sulfur. Accordingly, in this embodiment, the templating agent is formed in situ in the presence of the elemental sulfur with which it reacts in the step for reacting the templating agent with the elemental sulfur.

Polymeric sulfur was formed by reacting one mole of the (TMEDA)Zn(S$_6$) with one mole of oxidizing agent $Br_2$ to form a theoretical ½ mole of cyclododecasulfur compound. In another aspect, a substoichiometric (i.e. less than one equivalent) ratio of the oxidizing agent to the metallasulfur derivative may be selected in order to synthesize a cyclododecasulfur mixture having lower levels of halogens.

In another aspect, the metallasulfur derivative is a metallocene complex of titanium, zirconium, hafnium, iridium, or iron.

The methods of the present invention may be performed at a wide range of temperature, pressure, and concentration ranges. Suitable reaction temperatures are from −10° to 120° C., or between 0° C. and 100° C., more typically 3° to 90° C. When polymeric sulfur is the intended product, we have found it helpful to carry out the claimed invention at a temperature in excess of ambient temperature. While S12 may be preferentially produced at temperatures less than ambient, higher temperatures are preferably used when polymeric sulfur is the intended product.

However, the temperature at which polymeric sulfur begins to revert to S$_8$ defines an upper limit to the preferred temperature for production by the claimed invention. This temperature may be influenced by other materials in the reaction medium, some of which may initiate the reversion process. In general, the temperature is preferably less than about 100° C. More preferably the temperature should be less than 90° C. or less than 80° C. For example, the methods may be carried out at a temperature above ambient temperature, or a temperature of at least 25° C., or at least 30° C., or at least 40° C., or from about 25° C. to about 75° C., or from 30° C. to 70° C., or from 40° C. to 60° C. By ambient temperature we mean a comfortable temperature in which no extraordinary measures have been taken to raise or lower the temperature of the reaction zone from the temperature of the environment in which the reaction is carried out.

The metallasulfur derivative in the reacting step may be in any physical form desirable to facilitate the reaction. Suitable forms include solid, slurry in an appropriate solvent, or solution in an appropriate solvent. Accordingly, in one embodiment of the method of the present invention, the method includes forming a slurry of the metallasulfur derivative in a solvent prior to the reacting step. In another embodiment of the method of the present invention, the method includes forming a solution of the metallasulfur derivative in a solvent prior to the reacting step. When a slurry or solution form is utilized, typical metallasulfur derivative concentrations for the slurry or solution are 0.5 to 30 weight percent, more typically 2 to 25 weight percent, based on the total weight of the slurry or solution. Suitable solvents useful for the slurry or solution form in the reacting step include halogenated solvents of 1 to 12 carbon atoms and one halogen atom up to perhalogenated content. Examples of halogenated solvents include methylene chloride, chloroform, carbon tetrachloride, carbon tetrabromide, methylene bromide, bromoform, bromobenzene, chlorobenzene, chlorotoluenes, dichlorobenzenes, dibromobenzenes.

Other suitable solvents include alkanes of 5 to 20 carbons, aromatics, alkyl aromatics of 7 to 20 carbons. Examples are pentanes, hexanes, cyclohexane, heptanes, octanes, decanes, benzene, toluene, xylenes, mesitylene, ethyl benzene and the like. One or more combinations of solvents may also be utilized.

Similarly, the oxidizing agent in the reacting step may be in any physical form desirable to facilitate the reaction. Preferably, the oxidizing agent is in the form of a dispersion in a suitable dispersant. Accordingly, in one embodiment of the method of the present invention, the method includes forming a dispersion of the oxidizing agent in a dispersant prior to the reacting step. Typically, the oxidizing agent will be present in the dispersion in an amount of 0.5 to 60 wt % based on the total weight of the dispersion, more typically 1 to 25 wt % based on the total weight of the dispersion. Examples of dispersants include methylene chloride, chloroform, carbon tetrachloride, carbon tetrabromide, methylene bromide, bromoform, bromobenzene, chlorobenzene, chlorotoluenes, dichlorobenzenes, and dibromobenzenes.

In the method of the present invention, the step of reacting the metallasulfur derivative with the oxidizing agent is typically initiated and at least partially performed in a reaction zone. The reaction zone is generally defined as the volume or space wherein the step of reacting the metallasulfur derivative and the oxidizing agent commences and at least partially progresses toward completion. As the method of the present invention may be performed as a batch or semi-batch operation or continuous operation, and in any mode or reactor format known in the art including plug flow and stirred tank reactor constructions, the reaction zone may be configured according to factors such as for example capacity expectations; available manufacturing/plant area and capital; and utilities.

As the reaction of the reacting step is exothermic, the reacting step preferably includes removing heat of reaction from the reaction zone. In the embodiment wherein one or more of the metallasulfur derivative and the oxidizing agent are in a form that employs a solvent (slurry or solution for the metallasulfur derivative, or dispersant for the oxidizing agent), the heat removal step may include operating the step at a temperature and pressure to effect boiling of the solvent, solvents or dispersants. Alternatively, heat removal can be achieved by adding additional solvent or reactants into the reaction zone or by transferring heat from the reaction zone via a commercially available and well-known external heat exchange device such as a shell and tube or spiral wound heat exchanger.

The method of the present invention may be performed as a batch operation wherein reactants (metallasulfur derivative and oxidizing agent) are charged simultaneously or sequentially to the reaction zone. In one embodiment, wherein sequential addition of reactants is utilized, the reacting step of the method of the present invention may include first adding the oxidizing agent to the reaction zone then adding the metallasulfur derivative to the reaction zone. For sequential addition, the metallasulfur derivative may be in slurry or solution form and the oxidizing agent in dispersion form. In another embodiment, wherein simultaneous addition of reactants is utilized, the reacting step of the method of the present invention may include simultaneously adding the oxidizing agent and the metallasulfur derivative to the reaction zone.

Alternatively, the method of the present invention may be performed in plug-flow continuous mode, wherein reactants (metallasulfur derivative and oxidizing agent) are charged as separate continuous streams in such a manner to enhance mixing, such as impinging jets, into a static mixer, or a simple turbulent plug flow tubular reactor.

The reacting step of the present invention will typically extend for a period of from 30 seconds to 3 hours, preferably 1 minute to 2 hours and more preferably 2 minutes to 1 hour. When $(TMEDA)Zn(S_6)$ is utilized as the metallasulfur derivative and $Br_2$ is utilized as the oxidizing agent in the manufacture of polymeric sulfur, the reacting step of the present invention will typically extend for a period of from 1 minute to 1 hour, or from 5 minutes to 20 minutes. When $[PPh_4]_2[Zn(S_6)_2]$ is utilized as metallasulfur derivative and $Cl_2$ or $Br_2$ is utilized as the oxidizing agent, the reacting step of the present invention will typically extend for a period of 1 minute to 1 hour, or from 1 minute to 10 minutes.

The reacting step in the method of the present invention yields a polymer-containing reaction mixture. The reaction mixture typically contains the polymer, in amorphous or crystalline form, as the desired product, as well as one or more cyclic sulfur allotropes of small ring size (i.e., less than 25 sulfur atoms), solvents, dispersants, reaction byproducts, and unreacted reactants, generally referred to herein as "impurities" although they may have substantial commercial value, at least some of which may be insoluble in various solvents. Examples of impurities or byproducts are cyclooctasulfur and other allotropes of sulfur such as cyclohexasulfur, cycloheptasulfur, and cyclododecasulfur; unreacted oxidizing agent, metallasulfur derivative and its partially reacted derivatives or oligomers therein; ligand, such as TMEDA; metals, such as zinc, from the metallasulfur derivative synthesis; oxidant-sulfur derivatives, for example structures of the form $X—S_n—X$ where X is Cl or Br and n is greater or equal to 1; metal-containing compounds, such as $ZnBr_2$, $ZnCl_2$, $(TMEDA)ZnBr_2$, and $(TMEDA) ZnCl_2$; and any solvents used in the reaction or isolation steps. Accordingly, the method of the present invention may further include a process for isolating the polymeric sulfur from the polymeric sulfur-containing reaction mixture. Suitable techniques, methods and treatment steps for isolating the polymer from the polymer-containing mixture may vary widely depending on, for example, the choice of oxidizing agent, metallasulfur derivative, amount of unreacted reactants, the corresponding reaction efficiency, yield and the degree and the type of impurities and by-products and the like. The isolation process for polymer may comprise one or more of dissolving, drying, and sedimentation steps.

A dissolving step involves treating the polymer-containing mixture with a solvent which solubilizes impurities to form a dissolution liquor, followed by separating the dissolution liquor from the polymeric sulfur. Examples of "impurities" which may be separated from the polymer in a dissolution step are cyclic sulfur allotropes, for example cyclooctasufur, cyclohexasulfur, and cyclododecasulfur, metallasulfur derivatives, and metal-containing compounds. Separating the dissolution liquor from insoluble impurities may utilize separation techniques known in the art, such as filtration, centrifugation, or sedimentation. Typically, separating the dissolution liquor from polymer occurs at a temperature at or above that of the prior dissolution step to ensure that the impurities remain dissolved during the separation operation.

The solvent utilized in a dissolving step is preferably chosen from the group consisting of alkanes, halogenated hydrocarbons, aromatics, and carbon disulfide ($CS_2$). We note that the impurities, such as cyclosulfur allotropes, exhibit solubilities in various solvents that depend, in part, on the temperature, and that differ significantly from the solubility of polymeric sulfur. For example, depending on temperature, cyclooctasulfur is 30 to 200 times more soluble than cyclododecasulfur, and cyclododecasulfur is at least an order of magnitude more soluble than polymeric sulfur, in p-xylene, chlorobenzene, and $CS_2$ (see Example 5).

Preferred dissolving solvents are selected from the group consisting of $CS_2$, $C_5$ and larger alkanes, halogenated hydrocarbons of one to 12 carbon atoms and one halogen atom up to perhalogenated content. Examples of halogenated solvents include methylene chloride, chloroform, carbon tetrachloride, carbon tetrabromide, methylene bromide, bromoform, bromobenzene, chlorobenzene, chlorotoluenes, dichlorobenzenes, o-, m-, p-dibromobenzenes. Examples of alkane and aromatic dissolving solvents are o-, m-, p-xylenes, toluene, benzene, ethyl benzene, o-, m-, p-diisopropylbenzene, naphthalene, methyl naphthalenes, hexane and isomers, heptane and isomers, cyclohexane, methylcyclohexane, and decane.

Polymeric sulfur exhibits extremely low solubility in solvents, so the dissolution step is typically performed at an elevated temperature to minimize solvent usage and maximize impurity solubility, typically above −20° C. up to about 100° C. The solubilities of impurities vary considerably with the identity of the solvent, so the preferred temperature is dependent on the solvent chosen. For example, when using $CS_2$ as the solvent for the dissolving step, a preferred temperature range is −20 to 90° C., or from −10 to 70° C. When using alkanes, halogenated hydrocarbons or aromatics as the solvent for the dissolving step, a preferred temperature range is 15 to 100° C., or from 25 to 95° C. The weight ratio of dissolving solvent to polymer-containing mixture to be treated is typically about 500/1 to 1/1, more typically 300/1 to 10/1.

Surprisingly, differences in the density of impurities in the polymer-containing mixture and the polymer itself may be used to effect a purification of the polymer. In particular, polymer may be separated from metal particles, for example, zinc particles. In a sedimentation step, a polymer-containing mixture is contacted and mixed with a sedimentation solvent, causing suspension of particles within the sedimentation solvent resulting in a suspended slurry mixture. The suspended slurry mixture is then subjected to an external field of acceleration to effect a separation of types of particles into a settled particle layer and a suspended particle mixture. The external field of acceleration may be gravitational, centrifugal, magnetic, or electrostatic in nature.

For example, in the embodiment of the present invention wherein a crude polymer-containing mixture is produced from $Br_2$ oxidant and $(TMEDA)Zn(S_6)$ metallasulfur derivative, the polymer-containing mixture is subjected to a sedimentation step with $CS_2$ as the sedimentation solvent, forming a suspended slurry mixture. Agitation of the suspended slurry mixture is ceased, and the suspended slurry mixture is subjected to simple gravity sedimentation, resulting in a settled particle layer comprising polymer and large zinc particles, and a suspended particle mixture comprising mostly smaller zinc particles and sedimentation solvent. Decantation of the suspended particle mixture away from the selected particle layer results in reduction of the zinc content of the settled particle layer and enhancement of polymer content.

The sedimentation step may be operated in batch or continuous mode and may be repeated one or more times to enhance the separation. Preferred temperatures for the sedimentation step are between 0 and 80° C., more preferably 20 to 45° C.

The sedimentation solvent may comprise a liquid compound, dissolved cyclooctasulfur, or other soluble impurities from the crude polymer-containing mixture. Preferably the sedimentation solvent has a density greater than 1 g/cc and less than about 1.8 g/cc at the sedimentation step temperature. Examples of useful liquid compounds for use as a component of the sedimentation solvent are $CS_2$ and halogenated hydrocarbons of one to 12 carbon atoms and one halogen atom up to perhalogenated content. Examples of halogenated solvents include methylene chloride, chloroform, carbon tetrachloride, carbon tetrabromide, methylene bromide, bromoform, bromobenzene, chlorobenzene, chlorotoluenes, dichlorobenzenes, o-, m-, p-dibromobenzenes. The presence of dissolved cyclooctasulfur in the sedimentation solvent increases the density of the sedimentation solvent and is favored, in particular when suspending smaller metal particles. The preferred amount of dissolved cyclooctasulfur is dependent on the liquid compound used and sedimentation temperature, but typically is between about 1 wt % and 20 wt %.

As the product of other steps of the isolation process, such as dissolving and sedimentation, result in solvent-wet polymer particles, the isolating process may optionally include a step of drying the solvent-wet polymer particles to form dried polymer particles. Drying of the solvent-wet polymer particles may be accomplished by means known in the art, such as by inert gas sweep, heating, placing under vacuum, or combinations thereof. Typically, the drying step is accomplished at temperatures below the melting point of the polymer, more typically between about 20° C. and 90° C. at a pressure of less than 2 bara (bar absolute), typically at atmospheric pressure or down to about 0.05 bara.

A preferred isolating process for the method of the present invention includes (i) dissolving impurities from the polymer-containing mixture by treating the polymer-containing mixture with a solvent for the impurities to form a dissolution liquor, followed by separating polymer particles from the dissolution liquor; (ii) drying of the mother-liquor-wet polymer particles from step (i) to produce a purified polymer product.

In a second preferred embodiment, the isolating process includes (i) contacting the polymer-containing mixture with a sedimentation solvent to produce a suspended slurry mixture and a settled particle layer; (ii) dissolving impurities from the settled particle layer by treating the polymer-containing mixture with a solvent for the impurities to form a dissolution liquor, followed by separating polymer particles from the dissolution liquor; (iii) drying of the mother-liquor-wet polymer particles from step (ii) to produce a purified polymer product.

In a third preferred embodiment, the isolating process includes (i) dissolving impurities from the polymer-containing mixture by treating the polymer-containing mixture with a solvent for the impurities to form a dissolution liquor, followed by separating polymer particles from the dissolution liquor; (ii) contacting the polymer particles from the dissolution liquor of step (i) with a sedimentation solvent to produce a suspended slurry mixture and a settled particle layer; (iii) isolating the settled particle layer from step (ii) to produce a purified polymer product.

The following examples, while provided to illustrate with specificity and detail the many aspects and advantages of the present invention, are not be interpreted as in any way limiting its scope. Variations, modifications and adaptations which do depart from the spirit of the present invention will be readily appreciated by one of ordinary skill in the art.

Analytical Methods

Differential Scanning Calorimetry (DSC)—

The differential scanning calorimetry method (DSC) to measure the melting point range of the compounds of interest involves a first heating scan, from which are determined the melting peak temperature(Tm1) and the exothermic peak temperature (Tex1). The instrument used was a TA's Q2000 DSC (RCS) with a refrigerated cooling system. The procedure used is described herein as follows. The instrument was calibrated according to the manufacturers "User's Manual"; by setting the onset of the melting point of adamantane, indium and lead at −65.54° C., 156.60° C., and 327.47° C., respectively, and heat of fusion of Indium at 6.8 cal/g. A calibration specimen of about 3.0 mg was then scanned at a rate of 20° C./min. in the presence of helium with a flow rate of 50 cc/min. For sulfur-containing specimens, a similar method was used. A TA's Tzero aluminum pan and lid along with two aluminum hermetic lids were tared on a balance. About 3.0 mg of the sulfur-containing specimen was weighed into the Tzero pan, covered with the tared lid, and crimped using a TA's sample crimper with a pair of "Black" dies. The crimped specimen from the "Black" die stand was moved to the "Blue" die stand, where two tared hermetic lids were placed on the top of the specimen pan and crimped with the top "Blue" die. An empty crimped Tzero aluminum pan and lid along with 2 hermetic lids was prepared in a similar fashion as reference. The specimen and reference pans were placed in the DSC tray and cell at room temperature. After the DSC was cooled to −5° C. using a refrigerated cooling system, the specimen was heated from −5 to 200° C. at a rate of 20° C./min in the presence of helium. "Melt point onset" was defined as the temperature at the start of the endothermic melting event. Data analysis was performed using TA's software, Universal V4.7A, wherein, Tm1 refers to the low melting peak temperature occurring on the melting curve, using analysis option, "Signal Maximum". Tex1 refers to the exothermic peak temperature occurring right after Tm1, using analysis option, "Signal Maximum".

UniQuant (UQ)—

Samples were also analyzed using X-ray fluorescence and the UniQuant software package. UniQuant (UQ) is an x-ray fluorescence (XRF) analysis tool that affords standardless XRF analysis of samples. Samples can then be semi-quantitatively analyzed for up to 72 elements beginning with row three in the periodic table (i.e. Na to higher Z). The data are mathematically corrected for matrix differences between calibration standards and samples as well as absorption and enhancement effects; i.e. inter-element effects. Some factors that can affect the quality of results include granularity in the sample (leading to shadow effects), mineralogical effects (due to sample inhomogeneity), insufficient sample size, and lack of knowledge of the sample matrix. In cases where a sample was amenable to both, the XRF UQ analysis and the ICP-OES (i.e. quantitative) analysis generally agree within +/−10%. Samples were analyzed for Zn, Br, Cl, and S content by UQ.

ICP—

Approximately 100 milligrams of sample was weighed into a precleaned Quartz sample tube. Then 3 mL of concentrated nitric acid was added to each tube (Trace metal grade Fisher Chemical). Samples were microwave-digested using an Ultrawave Single Reaction Chamber Digestion System. After addition of scandium as an internal standard element (1 ppm level after final dilution), digested samples were diluted to a volume of 25 mL, yielding a final acid concentration of ~10% $HNO_3$ (based on nitric acid added and expected consumption of nitric acid during the digestion). A 1 ppm scandium internal standard was added to each sample. A Perkin Elmer Optima 2100 ICP-OES instrument (PerkinElmer Inc., Waltham Mass.) was calibrated with a matrix matched 1 ppm calibration standard and blank. Each sample, including a method blank was then analyzed for Zn, S, Br, and Cl content.

X-Ray Diffraction (XRD)—

Measurements were made on powder samples using a PANalytical Empyrean X-Ray Diffractometer (XRD) (Available from PANalytical Incorporated). The XRD utilized a Copper anode X-Ray Source operated at 45 kV and 40 mA. The system was configured for measurements in the Bragg Brentano θ/2θ reflection geometry. Diffraction measurements were collected from 5 to 90 degrees 2θ angle (two theta angle) with a sampling width of 0.026 degrees and a step time of ~160 sec. The sample was back-loaded into a 16 mm diameter powder sample holder and rotated during analysis on a spinner stage. The powder diffraction patterns for crystalline sulfur allotropes and polymeric sulfur were identified by comparison to patterns from a purchased database (International Centre for Diffraction Data ICDD, Newtown Square, Pa., USA or equivalent) or to patterns of known reference standards. Quantitation of crystalline sulfur allotropes and polymeric sulfur was performed by external calibration or the use of Reference Intensity Ratio (RIR) methodology.

Raman Spectroscopy—

The samples' Raman spectrum was measured using a Renishaw inVia confocal Raman microscope and WiRE 4.1 software with a 785 nm excitation laser and a 5× magnification microscope objective.

NMR—

Weigh approximately 0.0200 g of sample into a vial. Weigh approximately 0.0200 g of the internal standard, 1,4-dimethoxybenzene, into the same vial. Add approximately 1 mL of pyridine-d5, or other deuterated solvent that the material is soluble in. Take a $^1H$ NMR of the material and integrate the peak at δ 3.68 (6 protons). Integrate the two peaks at δ 2.45 and δ 2.25 (16 protons). Calculate the % purity using the following equation.

% Purity=100[(mg IS/MW IS)*(∫sample/∫IS)*(6/16)*
(MW sample/mg sample)]

IS=internal standard
MW=molecular weight
∫=value of the integration from the $^1H$ NMR Liquid Chromatography—

The liquid chromatography (LC) method separates elemental sulfur species including $S_8$ and $S_{12}$. The sulfur species were identified by retention time determined from known samples. The quantity of $S_8$ was determined by comparing the peak area of $S_8$ in the unknown sample with that of $S_8$ standard solutions of known concentrations made in toluene. The following operating parameters apply to all LC analyses:

HPLC instrument: Agilent 1200 with quaternary pump and diode array detector
Columns: Agilent, particle: Eclipse Plus C18, particle size: 3.5 um
Pre-column filter: Upchurch 0.5 um stainless steel frit, part no.: A316
Guard column: Phenomenex "security guard" HPLC guard cartridge system with C18 cartridge, part no.: KJ0-4282
Autosampler vials: from VWR, catalog number 500 779
Flow rate: 0.8 mL/min Run time: 40 min
Solvent: HPLC grade methanol isocratic
Column temperature: 6° C.
Detection wavelength: 254 nm, band width 16 nm
Injection volume: 5 uL

EXAMPLES

Preparation of a Cyclododecasulfur Compound from (TMEDA)Zn($S_6$)

Example 1. Preparation of Metallasulfur Derivative (TMEDA)Zn($S_6$)

Tetramethyl-ethylenediamine (TMEDA), (408 grams) and methanol (72 grams) were added to a 3 L, 3-neck glass flask equipped with a mechanical stirrer (reaching closely to the vessel walls), thermocouple, $N_2$ bubbler, water condenser, and electrical heating mantle. The system was purged with nitrogen and the temperature of the mixture adjusted to 35° C. Freshly ground cyclooctasulfur (powder) was added over five minutes while maintaining stirring at 425-450 rpm. The temperature was increased to 45° C. such that the freshly ground cyclooctasulfur was dissolved and whereupon 40 grams of metallic zinc powder (<10 micron particle size, >98% purity) was added over five minutes while maintaining stirring at 425-450 rpm. The gray-greenish yellow reactor contents were then heated slowly to 86° C. and agitated for 4 hours, or until yellow. Once yellow, the mixture was held for an additional two hours at temperature, with agitation. At the end of the reaction time, the flask was cooled to room temperature, the agitator turned off, and free liquid removed by vacuum extraction. Methanol (600 ml) was added to the flask to create a slurry, and agitated for one hour. The resulting slurry was then filtered on a vacuum Buchner filter (1 micron paper) and washed with two portions of 200 ml each of methanol. The solids were removed from the filter and dried overnight in a vacuum oven set at 50° C. and 0.1 MPa. Yield was near quantitative, with 233 grams of metallasulfur derivative (TMEDA)Zn($S_6$) complex, recovered at 97% purity as measured by NMR. Similar yields were uniformly achieved in multiple runs by carefully controlling mixing conditions.

Preparation of a Cyclododecasufur Compound ($S_{12}$) and Polymeric Sulfur.

Methylene chloride (750 mL) was added to a 2 L, 4-neck glass flask equipped with a mechanical stirrer, thermocouple, $N_2$ bubbler and stopper. Bromine (16.7 g, 104.5 mmol, 1.0 eq) as oxidizing agent was weighed into a bottle containing 50 mL $CH_2Cl_2$ and this mixture was added to the flask. The solution was cooled to 4° C. The zinc complex, (TMEDA)Zn($S_6$), from Example 1, (97.5% pure) (40 g, 104.3 mmol, 1.0 eq), was added all at once and washed in with 50 mL $CH_2Cl_2$. There was an immediate exotherm to 11° C. The solution was stirred for 15 minutes, filtered, washed with cold $CH_2Cl_2$ and suctioned dry. The solids were slurried in THF (250 mL), filtered and suctioned dry. The resultant solids were slurried in cold $CS_2$ (150 mL), filtered and suctioned dry to afford 10.2 g of a pale yellow solid. This process was repeated four times to afford a total of 42.69 grams of polymer-containing reaction mixture that included cyclododecasulfur.

The polymer was further isolated in a two-vessel system comprising an upper 1.5 L, jacketed 3-neck glass flask equipped with a mechanical stirrer, fine glass fritted filter plate, thermocouple, $N_2$ bubbler, dry ice trap, and bottom valve; and a lower 1.5 L, jacketed 3-neck glass flask equipped with a mechanical stirrer, water-cooled condenser and 1 L glass receiver pot, thermocouple, $N_2$ bubbler, dry ice trap, and bottom valve. To initiate the purification procedure, carbon disulfide (1000 grams) was added to the upper vessel along with the polymer-containing reaction mixture from the above reaction step (42.69 g). The contents of the flask were heated to 40-40° C. with stirring. After agitation of the mixture for half of an hour, the bottom valve of the vessel was opened, and the free liquid pulled through the fritted glass filter into the lower flask. About half of the initial solids remained on the filter. The solution in the second vessel was cooled to −6° C. over a period of 20 minutes or less. During the cooling phase, fine light yellow crystalline solids (cyclododecasulfur) were formed. The solution was stirred for about 15 minutes at a final temperature of −6° C., whereupon the bottom valve of the vessel was opened and the slurry of crystals-$CS_2$ was dropped onto a Buchner funnel fitted with 1 micron filter paper. The mother liquor from the final filtration was returned to the upper vessel, (containing residual solids), along with makeup $CS_2$ to give 1000 grams of liquid. The upper vessel was agitated and heated again to 40-42° C. and the filtering-cooling procedure was repeated until no more crystals were observed to form in the cooled $CS_2$. After the final heating-dissolution step, about 10 grams of yellow solids remained on the upper fritted filter. This material was placed in a vacuum oven overnight at 30° C. and about 0.01 MPa to remove residual $CS_2$. Raman analysis showed this material to be polymeric sulfur.

Example 2. Synthesis of (TMEDA)Zn($S_6$) with or without Water Addition

Tetramethyl-ethylenediamine (TMEDA), (2042 grams, 85 wt %, 99% pure, reagent plus grade) and methanol (360 grams, 15 wt %) were added to a 6 L, 4-neck jacketed glass reactor equipped with a mechanical stirrer (reaching closely to the vessel walls), thermocouple, $N_2$ bubbler, and water condenser. The system was purged with nitrogen and the temperature of the mixture was adjusted to 22° C. Freshly ground cyclooctasulfur powder (673 grams, ~90% pure) was added over a few minutes while maintaining a stirring speed of 425-450 rpm. To this suspension, metallic zinc (207 grams, 3.1 moles, <10 μm particle size, ≥98% pure) was added over five minutes while maintaining the same stirring speed. A brown solution resulted with some greenish precipitate after heating the reaction mixture for 2 hours at 86° C. This indicated that the reaction failed to produce the desired (TMEDA)Zn($S_6$) complex. At this point, 78 g of water was added to the reaction and the resulting mixture was heated to 86° C. for an additional 2 hours and yellow precipitate of (TMEDA)Zn($S_6$) formed. At the end of the reaction time, the flask was cooled to room temperature, the agitator was turned off, and free liquid was removed by vacuum extraction. Methanol (2000 ml) was added to the flask to create slurry and agitated for one hour. The resulting slurry was then filtered on a vacuum Buchner filter (1 micron paper) and washed with two portions of 600 ml each of methanol. The solids were removed from the filter and dried overnight in a vacuum oven set at 50° C. and 0.1 MPa. The corresponding yield was near quantitative, with 1087 grams of metallasulfur derivative (TMEDA)Zn($S_6$) complex, recovered at 97.5% purity as measured by NMR spectroscopy. Similar yields and purity were uniformly achieved in multiple runs under same reaction conditions. Addition of water consistently produced (TMEDA)Zn(S$_6$) complex in high yields and purity even with low grade TMEDA.

Example 3

Preparation of (TMEDA)Zn(S$_6$) with addition of water. Tetramethyl ethylenediamine (TMEDA), (2042 grams, 85 wt %, 99% pure, reagent plus grade), methanol (360 grams, 15 wt %), and water (78 grams) were added to a 6 L, 4-neck jacketed glass reactor equipped with two mechanical pitched blade agitators (reaching closely to the vessel walls), thermocouple, N$_2$ bubbler, and water condenser. The system was purged with nitrogen and the temperature of the mixture was adjusted to 22° C. Freshly ground cyclooctasulfur powder (673 grams, greater than 99% pure) was added over five minutes while maintaining a stirring speed of 425-450 rpm. To this suspension, metallic zinc (207 grams, 3.1 moles, <10 µm particle size, ≥98% pure) was added over five minutes while maintaining the same stirring speed. The greenish yellow mixture was then slowly heated to 86° C. and agitated for 2 hours, or until yellow precipitate appeared. Once the color turned yellow, the mixture was heated with stirring for an additional one hour. At the end of the reaction time, the flask was cooled to room temperature, the agitator was turned off, and free liquid was removed by vacuum extraction. Methanol (2000 ml) was added to the flask to create slurry and agitated for one hour. The resulting slurry was then filtered on a vacuum Buchner filter (1 micron paper) and washed with two portions of 600 ml each of methanol. The solids were removed from the filter and dried overnight in a vacuum oven set at 50° C. and 0.1 MPa. The corresponding molar yield on zinc metal was 90.1%, with 1087 grams of metallasulfur derivative (TMEDA)Zn(S$_6$) complex recovered at 98% purity as measured by NMR spectroscopy. Similar yields and purity were uniformly achieved in multiple runs under same reaction conditions Example 4. Solubility of Cyclooctasulfur, Cyclododecasulfur, and Crystalline Polymeric Sulfur in Carbon Disulfide, Chlorobenzene, and Para-Xylene Fifty grams of p-xylene was added to each of three identical 100-milliliter jacketed glass vessels fitted with a circulating heating bath, cooling water condenser, magnetic stir bar and stir plate, and nitrogen purge. All vessels were heated to the desired temperature, and cyclooctasulfur, cyclododecasulfur (prepared as in Example 2), and unoiled commercial crystalline polymeric sulfur (Crystex™) was added in sufficient quantities to each of the glass vessels to allow undissolved solids to remain after dissolution and equilibration of the mixture. The equilibration period typically lasted 2 to 8 hours, during which the contents of the vessel were maintained at the desired temperature and stirred continuously. Upon equilibration, supernatant liquid was withdrawn from the vessels via a heated fritted glass pipette (heated to the same temperature as the solution). The supernatants were analyzed by Uniquant to determine sulfur content, indicating the solubility of the sulfur species at the vessel temperature. Similar experiments were conducted for carbon disulfide and chlorobenzene for each of the three solutes. Solubilities in weight % of solute in each solvent are summarized in Table 4.

TABLE 4

| Solvent | Temperature, ° C. | Cyclooctasulfur | Cyclododecasulfur | Polymeric Sulfur |
|---|---|---|---|---|
| P-xylene | 22 | 2.3 wt % | Not measured | BDL* |
| | 45 | 5.6 wt % | <0.05 wt % | BDL* |
| | 115 | 18.7 wt % | 0.4 wt % | Decomposes to S$_8$ |
| Cl-benzene | 22 | 2.4 wt % | Not measured | BDL* |
| | 45 | 6.2 wt % | 0.015 wt % | BDL* |
| | 115 | 21.7 wt % | 0.44 wt % | Decomposes to S$_8$ |
| CS$_2$ | 22 | 32 wt % | 0.2 wt % | BDL* |
| | 45 | 48 wt % | 0.5 wt % | BDL* |

*BDL = below detection limit

Example 5

Preparation of Polymeric Sulfur via Bromination of (TMEDA)Zn(S6) Complex Under a High Zinc (wt %) Concentration. A three-necked round bottom flask was charged with (TMEDA)Zn(S6) (32 g, 83.9 mmol, 98% pure, 30 wt %) and dichloromethane (100 g, 1.177 mol). To this thick slurry, bromine (4.3 mL, 83.9 mmol, 1.0 eq) was added via a gas-tight syringe and the resulting mixture was stirred for 10 minutes at 0° C. The yellow solids were collected by vacuum filtration and thoroughly washed with acetone (3×50 mL) to remove residual (TMEDA)ZnBr$_2$ species. The dried material was slurried in chlorobenzene at 70° C. to solubilize cyclooctasulfur and cyclododecasulfur and this process was repeated three times. The insoluble solids were collected by filtration and suction dried to afford a pale greenish-yellow powder (~12% isolated yield). Raman spectroscopy and XRD analysis confirmed that the insoluble material consists of polymeric sulfur.

Example 6. Preparation of Polymeric Sulfur Via Controlled Chlorination of (TMEDA)Zn(S$_6$) Complex A three-necked round bottom flask was charged with (TMEDA)Zn(S$_6$) (15 g, 39.3 mmol, 98% pure, 15 wt %) and chlorobenzene. To this slurry, chlorine solution (39.3 mmol, 1.0 eq, 1(M) in chlorobenzene) was added via a gas-tight syringe and the resulting mixture was stirred for 10 minutes at 0° C. The solids were collected by vacuum filtration and throughly washed with acetone (3×50 mL) to remove residual (TMEDA)ZnCl$_2$ species. This material was further washed with CS$_2$ and THF at 0° C. to remove cyclooctasulfur and dried under vacuum to afford a pale yellow product (61% crude isolated yield). Raman spectroscopy and XRD analysis showed the material is a mixture of cyclododecasulfur and polymeric sulfur.

Example 7. Preparation of Polymeric Sulfur Via Reverse-Order Bromination of (TMEDA)Zn(S$_6$) Complex A three-necked round bottom flask was charged with chlorobenzene (400 mL) and bromine (4.3 mL, 83.9 mmol). To this orange solution, solid (TMEDA)Zn(S$_6$) (32 g, 83.9 mmol, 98% pure) was added all at once and the resulting mixture was stirred for 10 minutes at 0° C. The solids were collected by vacuum filtration and throughly washed with acetone (3×50 mL) to remove residual (TMEDA)ZnBr$_2$ species. The dried material was slurried in chlorobenzene at 70° C. to solubilize cyclooctasulfur and cyclododecasulfur and this process of repeated three times. The insoluble solids were collected by filtration and suction dried to afford a pale greenish-yellow powder (~9% isolated yield). Raman spectroscopy and XRD analysis confirmed that the insoluble material consists of polymeric sulfur.

Example 8. Preparation of $Cp_2Ti(S_5)$ Complex

Titanocene chloride solution was prepared by dissolving 23 grams of titanocene dichloride (>99% purity) in flask containing 1110 grams of chloroform heated to 40° C. 23 grams of flake sulfur was added to a 2-liter glass round bottom flask (fitted with a cooling water condenser, mechanical crescent-bladed agitator, and $N_2$ purge) containing 100 grams of 40 wt % aqueous ammonium sulfide. The flask was stirred until all sulfur dissolved (approximately 1 hour). Next, the entire titanocene dichloride solution prepared previously was added to the 2-liter vessel with stirring and held overnight. Once the reaction was complete, the entire contents of the reaction vessel were transferred to a 3-liter separatory funnel and allowed to separate into two phases. The water layer was drained from the separatory funnel and the organic layer was washed with 4 portions 500 grams of water. The red organic layer was set aside for later processing. All of the aqueous layers (including initial reaction layer and all water washes) were combined and extracted five times with 500 grams of fresh chloroform. All chloroform layers were combined and rotovapped to dryness at 60° C. and 200 torr. The resulting solids were dried under vacuum at 75° C. overnight, to give 29 grams of titanocene pentasulfide (93% of theoretical yield).

Example 9. Preparation of Polymeric Sulfur Via Bromination of $Cp_2Ti(S_5)$ Complex in Dichloromethane A three-necked round bottom flask was charged with $Cp_2Ti(S_5)$ (10 g, 29.7 mmol) and dichloromethane (191 mL, 2.973 mol). To this solution, bromine (1.5 mL, 29.7 mmol, 1.0 eq) was added via a gas-tight syringe and the resulting mixture was stirred for 10 minutes at 0° C. The solids were collected by vacuum filtration and throughly washed with acetone (3×50 mL) and dichloromethane to remove residual $Cp_2TiBr_2$ species. The dried material was slurried in chlorobenzene at 70° C. to solubilize cyclosulfur allotropes and this process was repeated three times. The insoluble solids were collected by filtration and suction dried to afford a powder (14% isolated yield), confirmed to be polymer by XRD and Raman spectroscopy.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A method for the manufacture of polymeric sulfur, comprising reacting a metallasulfur derivative with an oxidizing agent in a reaction zone to form polymeric sulfur in a polymeric sulfur-containing reaction mixture.

2. The method of claim 1, wherein the metallasulfur derivative is characterized by the formula;

$$-\!\!\left[\mathrm{L}_x\mathrm{M}_y\mathrm{S}_z\right]^u_v\!\!- \quad [\mathrm{I}]_w$$

wherein
L is a monodentate or polydentate ligand species which may be the same or different when x>1;
x is the total number of ligand species and is from 0 to 6 inclusive;
M is a metal atom;
y is the total number of metal atoms and is from 1 to 4 inclusive;
S is a sulfur atom;
z is the number of sulfur atoms, and is from 1 to 12 inclusive;
u represents the charge of the metallasulfur derivative and may be from −6 to +6 inclusive;
v is the number of metallasulfur derivative units in an oligomeric or polymeric structure;
I is an ionic atom or group and may be cationic or anionic;
and w is the number of cationic or anionic atoms or groups, as required to provide charge neutrality.

3. The method of claim 2, wherein the oxidizing agent is characterized by the formula:

$$\mathrm{X}\!\!-\!\!\mathrm{X}'$$

wherein X and X' are the same or different and are selected from the group consisting of halogens and pseudohalogens.

4. The method of claim 3, wherein the stoichiometric ratio of the oxidizing agent to the metallasulfur derivative is selected so that less than one equivalent of the oxidizing agent is present for every two M-S bonds in the metallasulfur derivative.

5. The method of claim 3, wherein X and X' are chlorine or bromine.

6. The method claim 1, wherein the reacting is carried out at a temperature greater than ambient temperature.

7. The method claim 1, wherein the reacting is carried out at a temperature from about 40° C. to about 60° C.

8. The method of claim 1, further comprising reacting elemental sulfur with a sulfur templating agent to form the metallasulfur derivative prior to the step of reacting the metallasulfur derivative with the oxidizing agent.

9. The method of claim 1, further comprising isolating the polymer from the polymer-containing reaction mixture by:
(i) dissolving impurities from the polymer-containing mixture by treating the polymer-containing mixture with a solvent for the impurities to form a dissolution liquor, followed by separating polymer particles from the dissolution liquor to obtain mother-liquor-wet polymer particles; and
(ii) drying the mother-liquor-wet polymer particles from step (i) to produce purified polymer.

10. The method of claim 1, further comprising isolating the polymer from the polymer-containing reaction mixture by:
(i) contacting the polymer-containing mixture with a sedimentation solvent to produce a suspended slurry mixture and a settled particle layer;

(ii) dissolving impurities from the settled particle layer by treating the settled particle layer with a solvent for the impurities to form a dissolution liquor, followed by separating polymer particles from the dissolution liquor to obtain mother-liquor-wet particles; and (iii) drying the mother-liquor-wet polymer particles to produce purified polymer.

11. The method of claim 1, further comprising isolating the polymer from the polymer-containing reaction mixture by:

(i) dissolving impurities from the polymer-containing mixture by treating the polymer-containing mixture with a solvent for the impurities to form a dissolution liquor, followed by separating polymer particles from the dissolution liquor;

(ii) contacting the polymer particles with a sedimentation solvent to produce a suspended slurry mixture and a settled particle layer; and (iii) separating the settled particle layer from the suspended slurry mixture to obtain purified polymer.

12. The method of claim 8, further comprising forming a slurry of the sulfur templating agent in a solvent prior to the reacting step.

13. The method of claim 8, further comprising forming a solution of the sulfur templating agent in a solvent prior to the reacting step.

14. A method for the manufacture of a polymeric sulfur compound, the method comprising:

(i) reacting cyclooctasulfur, tetramethylethylenediamine, and zinc in the presence of water to form a tetramethylethylenediamine/$Zn(S_6)$ complex; and (ii) reacting the complex with an oxidizing agent in the presence of a solvent for the complex at a temperature greater than ambient temperature.

* * * * *